US00PP25938P2

(12) United States Plant Patent
Fitzgerald

(10) Patent No.: US PP25,938 P2
(45) Date of Patent: Sep. 22, 2015

(54) ***CAREX* PLANT NAMED 'EVERSHEEN'**

(50) Latin Name: *Carex oshimensis*
Varietal Denomination: Eversheen

(71) Applicant: Garraith Ltd, Old Town (IE)

(72) Inventor: Pat Fitzgerald, Old Town (IE)

(73) Assignee: GARRAITH LTD., Old Town (IE)

( * ) Notice: Subject to any disclaimer, the term of this patent is extended or adjusted under 35 U.S.C. 154(b) by 155 days.

(21) Appl. No.: 13/998,173

(22) Filed: Oct. 7, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Anne Grunberg
(74) *Attorney, Agent, or Firm* — Penny J. Aguirre

(57) ABSTRACT

A new cultivar of *Carex oshimensis*, 'Eversheen', characterized its dwarf plant habit, its foliage that is variegated with green-yellow centers and deep green margins, and its robust growth habit.

3 Drawing Sheets

Botanical classification: *Carex oshimensis.*
Varietal denomination: 'Eversheen'.

BACKGROUND OF THE INVENTION

The present invention relates to a new and distinct cultivar of *Carex oshimensis* and will be referred to hereafter by its cultivar name, 'Eversheen'. 'Eversheen' is a new cultivar of perennial ornamental grass grown for container and landscape use, primarily in shaded exposures.

The new cultivar, 'Eversheen' arose as a naturally occurring chimeral mutation of *Carex oshimensis* 'Evergold' (not patented). The Inventor discovered 'Eversheen' in August of 2008 in a container at his nursery in Oldtown, Stoneyford, Co. Kilkenny, Republic of Ireland.

Asexual propagation of the new cultivar was first accomplished by rhizome division in Oldtown, Stoneyford, Co. Kilkenny, Republic of Ireland in 2008 by the Inventor. Asexual propagation of the new cultivar by rhizome division and basal cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'Eversheen' as a distinct cultivar of *Carex.*

1. 'Eversheen' exhibits a dwarf plant habit.
2. 'Eversheen' exhibits foliage that is variegated with green-yellow centers and deep green margins.
3. 'Eversheen' exhibits a robust growth habit.

'Evergold', the parent plant of 'Eversheen', differs from 'Eversheen' in having foliage that is variegated with creamy-yellow centers and green margins. 'Eversheen' can be most closely compared to the cultivar 'Everillo' (U.S. Plant Pat. No. 21,002) and 'Everoro' (U.S. Plant Pat. No. 23,406). 'Everillo' differs from 'Eversheen' in having foliage that is solid yellow in color. 'Everoro' differs from 'Eversheen' in having foliage that is variegated with golden yellow centers and green margins.

BRIEF DESCRIPTION OF THE DRAWINGS

The accompanying colored photographs illustrate the overall appearance and distinct characteristics of the new *Carex.*

The photographs in FIG. 1 and FIG. 2 were taken of a six month-old plant the new *Carex* as grown outdoors in a 17-cm container in Oldtown, Stoneyford, C. Kilkenny, Ireland. The photograph in FIG. 1 illustrates the dwarf plant habit and appearance of 'Eversheen'. The photograph in FIG. 2 provides a close-up view of the foliage of 'Eversheen'.

Figure 1:
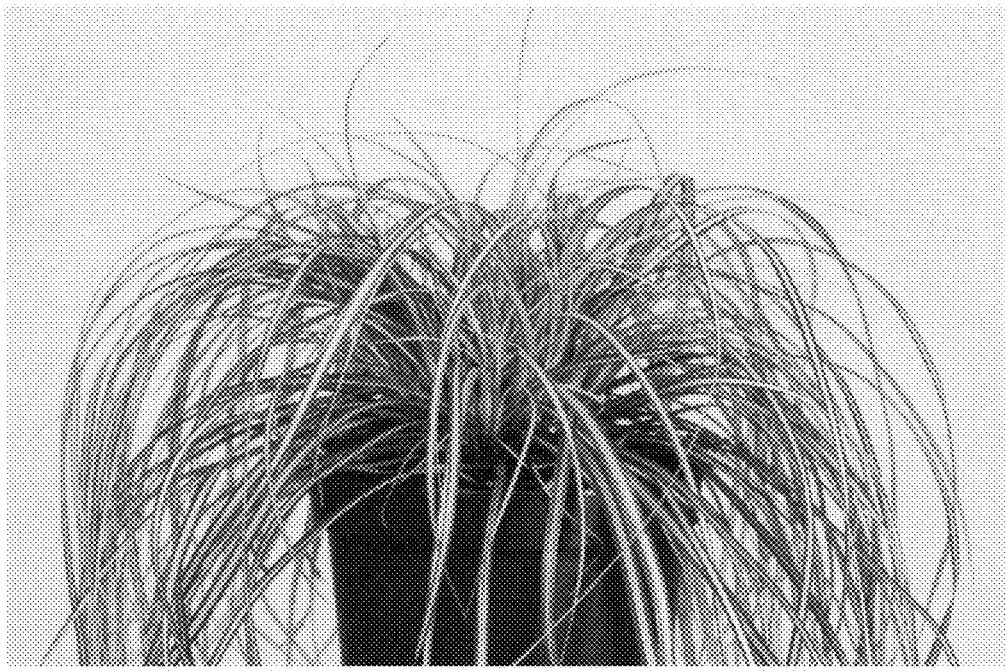
Figure 2:
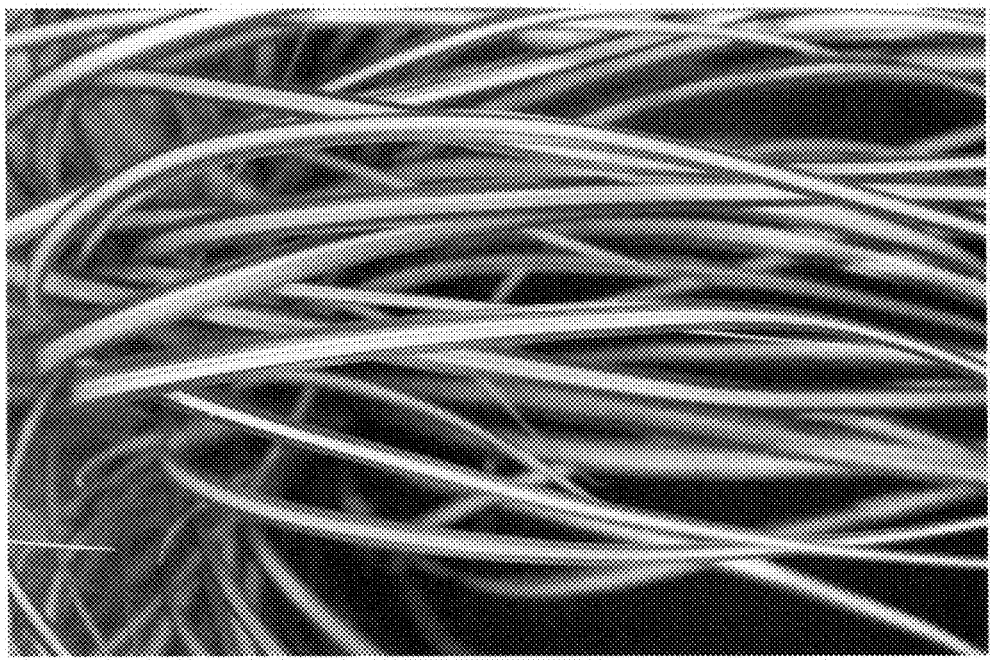
Figure 3:
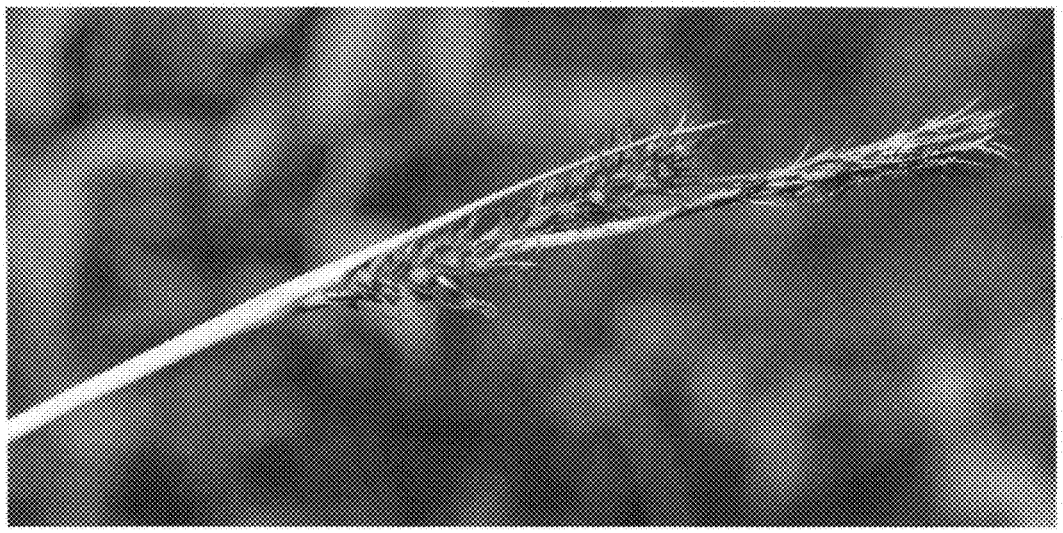

The photograph in FIG. 3 was taken of a one year-old plant as grown in a garden in Oldtown, Stoneyford, C. Kilkenny, Ireland and provides a view of inflorescences of 'Eversheen'.

The colors in the photographs may differ slightly from the color values cited in the detailed botanical description, which accurately describe the colors of the new *Carex.*

DETAILED BOTANICAL DESCRIPTION

The following is a detailed description of six month-old plants as grown outdoors in a nursery in 17-cm containers in Co. Kilkenny, Republic of Ireland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Inflorescences emerge the end of Februrary and continue into mid summer in the Republic of Ireland.

*Plant habit.*—Herbaceous perennial, flattened globular with arching leaves and inflorescences.

*Growth habit.*—Broad, spreading.

*Height and spread.*—Reaches an average of 23.3 cm in height above pot (cascading from top of plant towards base of pot 43 cm), spreads to an average of 37.5 cm in diameter.

*Hardiness.*—At least in U.S.D.A. Zones 6.

*Plant vigor.*—Moderate.

*Diseases and pests.*—No observed susceptibility or resistance to pests and diseases.

*Root description.*—Short, stout rhizomes with dense, fibrous roots, roots moderately branched.

*Propagation.*—Rhizome division and basal cuttings.

*Branching.*—Average of 38 main shoots grow from the base, no lateral branches.

Foliage description:

*Leaf shape.*—Linear.

*Leaf division.*—Simple.

*Leaf base.*—Sheathing.

*Leaf apex.*—Long acuminate.

*Leaf aspect.*—Leaves initially emerge upright, then cascade outward and finally arch downward until the terminal blades lay on the ground.

*Leaf venation.*—Parallel.

*Leaf margins.*—Entire and moderately sharp when rubbed downwards due to very small teeth too small to be seen or measured.

*Leaf size.*—Matures to an average of 39.8 cm in length and 7 mm in width.

*Leaf number.*—Average of 10 leaves per shoot.

*Leaf arrangement.*—Alternate.

*Leaf surface.*—Upper surface glossy and glaborous, lower surface moderately glossy and glabrous.

*Leaf color.*—Young upper surface; centers a color between 145A to 149A, margins 137A and 143A, young lower surface; centers a color between 145A to 149A, margins 143A, mature upper surface; centers N144D, margins a color between 137A and 139A, mature lower surface; centers a blend of 144C to N144, margins a color between 137A an 139A.

*Durability to stresses.*—High.

*Petiole.*—No petioles, leaves sheathing; average length of sheath of 2.2 and average diameter 4 mm, 177C with stripes N200A in color.

Flower description:

*General description.*—Terminal racemes, male and female flowers on separate spikelets.

*Inflorescence size.*—Average of 7 cm in height and 1.8 cm in width.

*Flower quantity per inflorescence.*—Average of 40 male flowers placed in an average of 1 spikelet and an average of 38 female flowers placed in an average of 2 spikelets.

*Lastingness of inflorescence.*—Flowers last about 10 days.

*Flowering season.*—Continuous from late winter into summer.

*Response time to flower.*—Approximately 8 months.

*Rate of flower opening.*—After first initial flowers open in an inflorescence all flowers open within 3 weeks.

*Fragrance.*—None.

*Flower buds.*—Male flower: average of 0.5 cm in length and 2 mm in diameter, narrow oblong in shape and 199C in color, female flower: average of 0.4 cm in length and 2 mm in width, narrow obovate in shape and 147D in color.

*Spikelet shape.*—Sedge-like, narrowly ovate.

*Persistence of spikelets.*—Persistant.

*Floret (spikelet) size.*—Staminate florets; an average of 2 mm in diameter and 7 mm in length, pistillate florets; an average of 3 mm in diameter and 5.5 mm in length.

*Floret (spikelet) description.*—1 glume on inner side and 1 lemma on outer side, male flower: average of 1 glume and 1 lemma, glume and lemma surfaces smooth and dull, glume and lemma lanceolate in shape, glume and lemma entire margin, glume apex long, narrow and acute, lemma apex long mucronate, glume and lemma 8 mm in length and 1 mm in width, glume and lemma color: upper and lower surface when opening and fully open; N199C to N199D, female flower: (no glume), lemma; 1, smooth and dull surfaces, lanceolate in shape, entire margin, apex long mucronate, average of 5.5 mm in length and 1 mm in width, color: upper and lower surface when opening and fully open; 145A.

*Peduncle.*—An average of 20 cm in length and 1.5 mm in diameter, held upright to 10° to upright, strong, 143A in color.

Reproductive organs:

*Gynoecium.*—Average of 1 pistil about 3 mm in length, stigma is fimbriate and 156D in color, style is about 0.5 mm in length and 144B in color, ovary is 144D in color.

*Androcoecium.*—Average of 3 stamens, basifixed, about 2 mm in length and 162B in color, pollen production very low and insufficient in quantity to be color coded.

*Fruits and seeds.*—Seed production has not been observed to date.

It is claimed:

1. A new and distinct cultivar of *Carex* plant named 'Eversheen' as herein illustrated and described.

* * * * *